United States Patent
Pullagurla et al.

(10) Patent No.: US 9,963,422 B2
(45) Date of Patent: May 8, 2018

(54) PROCESS FOR THE SYNTHESIS OF MELPHALAN AND THE HYDROCHLORIDE SALT

(71) Applicant: Biophore India Pharmaceuticals PVT. Ltd., Hyderabad (IN)

(72) Inventors: Manik Reddy Pullagurla, Hyderabad (IN); Jagadeesh Babu Rangisetty, Hyderabad (IN); Mecheril Valsan Nandakumar, Hyderabad (IN); Madhava Reddy Vedururi, Hyderabad (IN); Sreenu Samireddi, Hyderabad (IN)

(73) Assignee: Biophore India Pharmaceuticals PVT. Ltd., Hyderabad (IN)

( * ) Notice: Subject to any disclaimer, the term of this patent is extended or adjusted under 35 U.S.C. 154(b) by 4 days.

(21) Appl. No.: 14/764,183

(22) PCT Filed: Mar. 4, 2014

(86) PCT No.: PCT/IN2014/000141
§ 371 (c)(1),
(2) Date: Jul. 29, 2015

(87) PCT Pub. No.: WO2014/141294
PCT Pub. Date: Sep. 18, 2014

(65) Prior Publication Data
US 2016/0016889 A1    Jan. 21, 2016

(30) Foreign Application Priority Data
Mar. 11, 2013   (IN) .......................... 1018/CHE/2013

(51) Int. Cl.
| | | |
|---|---|---|
| *C07C 269/06* | (2006.01) |
| *C07C 227/12* | (2006.01) |
| *C07C 227/20* | (2006.01) |
| *C07C 227/40* | (2006.01) |
| *C07C 229/42* | (2006.01) |
| *C07C 231/12* | (2006.01) |

(52) U.S. Cl.
CPC .......... *C07C 227/12* (2013.01); *C07C 227/20* (2013.01); *C07C 227/40* (2013.01); *C07C 229/42* (2013.01); *C07C 231/12* (2013.01); *C07C 269/06* (2013.01); *C07B 2200/07* (2013.01)

(58) Field of Classification Search
None
See application file for complete search history.

(56) References Cited

U.S. PATENT DOCUMENTS

2009/0240074 A1* 9/2009 Jobdevairakkam ... C07C 227/18
560/40
2012/0116117 A1  5/2012 Gurjar et al.

OTHER PUBLICATIONS

Fernando Albericio et al. Chem. Rev. 2009, 109, 2455-2504; Amino Acid-Protecting Groups. (para 2.1).

* cited by examiner

*Primary Examiner* — Sudhakar Katakam
*Assistant Examiner* — Jennifer C Sawyer

(57) ABSTRACT

The present invention relates to an improved process for the preparation of Melphalan, more specifically the invention relates to an efficient process for the preparation of substantially pure Melphalan hydrochloride (I).

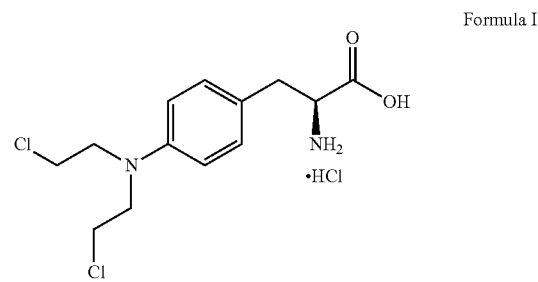

Formula I

4 Claims, No Drawings

PROCESS FOR THE SYNTHESIS OF MELPHALAN AND THE HYDROCHLORIDE SALT

FIELD OF INVENTION

The invention relates to a novel process for preparation of Melphalan hydrochloride of Formula-I, in a substantially pure form for the treatment of multiple myeloma and ovarian cancer.

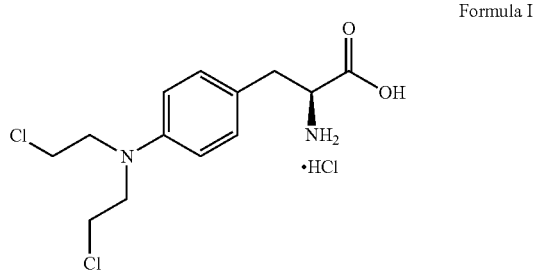 [SMILES: N[C@@H](Cc1ccc(N(CCCl)CCCl)cc1)C(=O)O ; Cl]

Formula I

BACKGROUND OF THE INVENTION

Melphalan is chemically known as 4-[bis(chloroethyl)amino]phenylalanine and also by other names like L-phenylalanine mustard, phenylalanine mustard, L-PAM, or L-sarcolysin. It is a phenylalanine derivative of nitrogen mustard. Melphalan is a bifunctional alkylating agent which is active against selective human neoplastic diseases.

Melphalan is marketed as its hydrochloride salt under the brand name ALKERAN. The synthesis of Melphalan was first disclosed in U.S. Pat. No. 3,032,584 and U.S. Pat. No. 3,032,585.

The following patents and applications describe the synthesis of Melphalan hydrochloride. U.S. Pat. No. 3,032,584 and U.S. Pat. No. 3,032,585 describe process for the production of melphalan free base by protecting glycinic amino group (P-nitro-L-phenyl alanine) with phthalimide functional group followed by esterification to produce ester compound of P-nitro-N-phthaloyl-L-phenyl alanine. Ester derivative of P-nitro-N-phthaloyl-L-phenyl alanine is then subjected to catalytic hydrogenation to reduce nitro group to an amino group, treating the amino compound with ethylene oxide to affect the bishydroxyethylation. The product is then subjected to chlorination followed by hydrolysis and deprotection of the phthaloyl group to produce L-4-[bis(2-chloroethyl)-amino]-phenylalanine.

European patent EP0233733 discloses the process for making L-4-[bis(2-chloroethyl)-amino]-phenylalanine by using phthalimide group to protect glycinic amino group of 4-nitro phenylalanine ethyl ester.

These patents do not disclose a method for isolating the acid addition salts of the L-form of 4-[bis(2-chloroethyl)-amino]-phenylalanine, specifically the hydrochloride salt.

U.S. Pat. No. 4,997,651 discloses a method for preparing melphalan hydrochloride comprising addition of hydrochloric acid to slurry of melphalan free base in an alcohol, preferably ethanol and refluxing the mixture for minimum duration to reduce the level of impurities. Using an alcohol solvent for preparation of the hydrochloride salt results in the formation of the corresponding ester and removal of which could result in lower yield and is tedious process. Complete conversion of free base to hydrochloride salt in a short time on large scale is difficult with alcohol solvents. And the purity reported by HPLC was 97.5%.

RO 57195 describes a method for purification of melphalan free base through formation of the hydrochloride salt followed by treatment with a suitable base such as sodium bicarbonate or sodium acetate.

US2009/240074 A1 describes the synthesis of optically pure 4-(bis-(2-hydroxyethyl)amino)-L-phenylalanine by hydroxyethylation, in a regioselective manner, of the aromatic amino group in presence of a free glycinic amino group. 4-(Bis-(2-hydroxyethyl)amino)-L-phenylalanine was converted to melphalan in presence of $POCl_3$ and when isolated as a sulfate salt a purity of 96% was obtained. Isolation of Melphalan freebase from concentrated HCl reaction mass required distillation of HCl followed by pH adjustment.

Melphalan crudes obtained were converted into hydrochloride salt in water followed by in situ conversion of the hydrochloride salt to free base by pH adjustment. The purity of the free base obtained was 99%. The process required tedious workup to obtain Melphalan.

US 20120116117 describes a process for the preparation of Melphalan HCl, comprising treatment of 4-[bis(2-chloroethyl)-amino]-L-phenylalanine in conc. hydrochloric acid and isolating the obtained 4-[bis(2-chloroethyl)-amino]-L-phenylalanine hydrochloride by azeotropic distillation of the water in presence of toluene and isolation of the product with isopropyl alcohol to obtain the Melphalan HCl with a purity of >99.0% It is clearly evident from the above prior art that the product obtained by known methods generate associated impurities and require extensive purifications. Therefore, to overcome the problems associated with prior art, there is a need to develop an efficient and cost effective method for the synthesis of Melphalan hydrochloride and which can be easily converted to the free base in its pure form.

OBJECTS OF THE INVENTION

One object of the invention is to provide an efficient method for the synthesis of substantially pure Melphalan HCl with >99.5% HPLC purity.

Another object of the invention is to provide a process which is commercially viable for the synthesis of the pure Melphalan HCl.

Yet another object of the invention is to provide a process for obtaining Melphalan freebase with good purity from a pure Melphalan HCl

SUMMARY OF THE INVENTION

Accordingly the present invention provides a novel process for preparation of Melphalan hydrochloride of Formula-I, having greater than 99.5% HPLC purity.

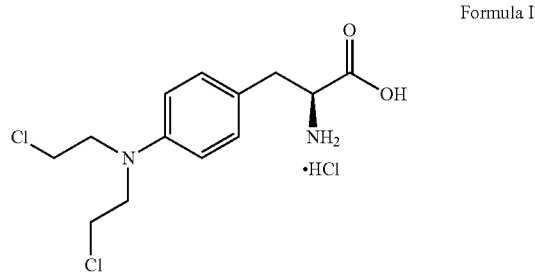 [SMILES: N[C@@H](Cc1ccc(N(CCCl)CCCl)cc1)C(=O)O ; Cl]

Formula I

In one embodiment the invention provides a process for preparation of Melphalan hydrochloride of Formula-I comprising the steps of:

a) chlorinating a compound of formula III

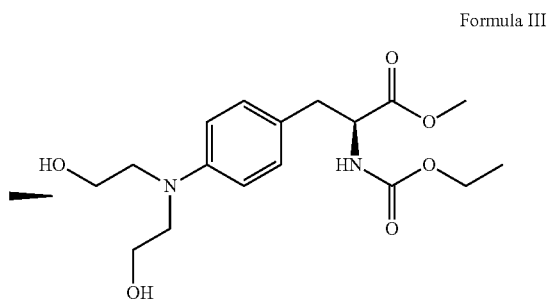

Formula III with thionyl chloride or POCl$_3$ to obtain a compound of formula IV;

Formula IV b) treating the compound of formula IV with Conc. HCl to hydrolyze the amino and acid protecting groups;
c) adjusting the pH of the aqueous medium to 0.3 to 1.2;
d) extracting into an organic solvent and isolating the pure Melphalan Hydrochloride of Formula-I;

Formula I e) optionally, purifying the Melphalan Hydrochloride;
f) optionally, converting the Melphalan Hydrochloride in Melphalan free base.

The organic solvent for extraction is selected from the group comprising ethyl acetate, isopropyl acetate, isobutyl acetate, acetonitrile, dioxane or mixtures thereof.

In another embodiment, the invention provides a process for purification of Melphalan Hydrochloride comprising the steps of:
a). dissolving Melphalan hydrochloride of low purity in aqueous hydrochloric acid;
b). adjusting the pH of the aqueous medium to 0.3 to 1.2;
c). extracting into an organic solvent and isolating the substantially pure Melphalan Hydrochloride;

The organic solvent used in the purification process is ethylacetate.

DETAILED DESCRIPTION OF THE INVENTION

Detailed embodiments of the present invention are disclosed herein below. However, it is to be understood that the disclosed embodiments are merely exemplary of the invention, which can be embodied in various forms. The scope of the invention is not limited to the disclosed embodiments and terms and phrases used herein are not intended to be limiting but rather to provide an understandable description of the invention. The invention is defined by claims appended hereto.

The invention provides a novel process for preparation of Melphalan hydrochloride of Formula-I, having greater than 99.5% HPLC purity.

Formula I

Preparation of Compound of Formula III

Compound of Formula II is converted to compound of Formula III in presence of ethylene oxide in water and followed by recrystallization to provide a compound of formula III in >98% HPLC purity. The conversion of compound II to compound III can also be carried out in presence of an organic or inorganic base and in 2-chloroethanol.

Formula II

Formula III

Preparation of Compound of Formula I

Compound of Formula III in presence of POCl3 or thionyl chloride is converted to compound of Formula IV after which the solvent is completely distilled off.

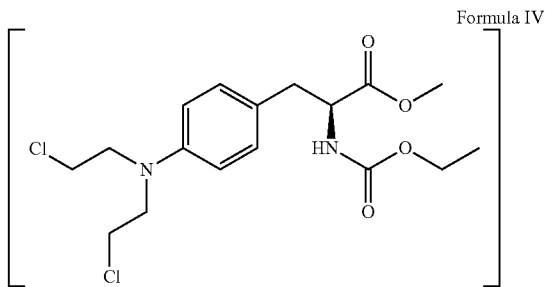

Formula IV

The hydrolysis of the protection groups on the amine and carboxylic acid is performed in concentrated hydrochloric acid. The obtained reaction mass is extracted with an organic solvent and then the aqueous layer is treated with carbon to provide a solution with significantly improved color.

The pH of the aqueous acidic solution is adjusted with a solution of sodium bicarbonate or the like to 0.3 to 1.2. The purity and the yield of the Melphalan Hydrochloride isolated depends on the pH of the aqueous medium. After the pH of the solution is adjusted to the said desired range, Melphalan in its hydrochloride form is extracted into the organic solvent. The organic solvents that can be employed are ethyl acetate, isopropyl acetate, isobutyl acetate, acetonitrile, dioxane or the like, ethyl acetate being the most preferred solvent.

Melphalan Hydrochloride is an unstable compound and increase in temperature may lead to decomposition of the compound. However, under the given parameters of the invention, the organic solution is distilled at temperatures of 25-65° C., without affecting the purity of the compound (>99.5%). The product may optionally be slurried in an aprotic solvent such as acetone, MTBE, dichloromethane and preferably acetone and the compound filtered to give a substantially pure Melphalan HCl.

Inventors have thus found a novel method for isolating Melphalan hydrochloride directly by extracting it into a suitable solvent from an aqueous solution of the hydrochloride salt of Melphalan. The purity of the hydrochloride salt is >99.5%, with monohydroxyMelphalan below 0.15%, dihydroxyMelphalan below 0.1% Melphalan dimer below 0.15%. 1 OH

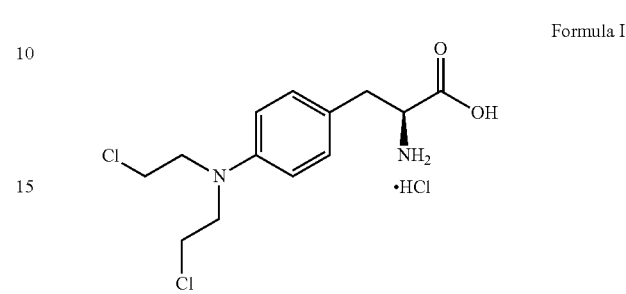

Formula I

The present inventors have found yet another novel method of purification of low purity Melphalan Hydrochloride or free base by converting to pure Melphalan Hydrochloride. The process involves dissolving Melphalan hydrochloride of any purity in aqueous hydrochloride solution, adjusting the pH to 0.3 to 1.2 followed by extraction with organic solvents like ethyl acetate, isopropyl acetate, isobutyl acetate, acetonitrile, dioxane or the like, ethyl acetate being the preferred solvent. The organic solvent is distilled at temperatures of 25-65° C. to give Melphalan hydrochloride salt with >99.5% HPLC purity, any single impurity of less than 0.15% (monohydroxymelphalan below 0.15%, dihydroxymelphalan below 0.1% Melphalan dimer below 0.15%).

Preparation of Compound of Formula V

Melphalan HCl in its substantially pure form can be converted to Melphalan Free Base by pH adjustment to 3 to 5 in water with a basic solution of sodium bicarbonate or the like at about 5° C. to provide the free base with >99.3% purity and the monohydroxymelphalan below 0.15% and dihydroxymelphalan below 0.1%.

The process of the invention is illustrated below in Scheme-I and further illustrated by the following examples.

Scheme-I

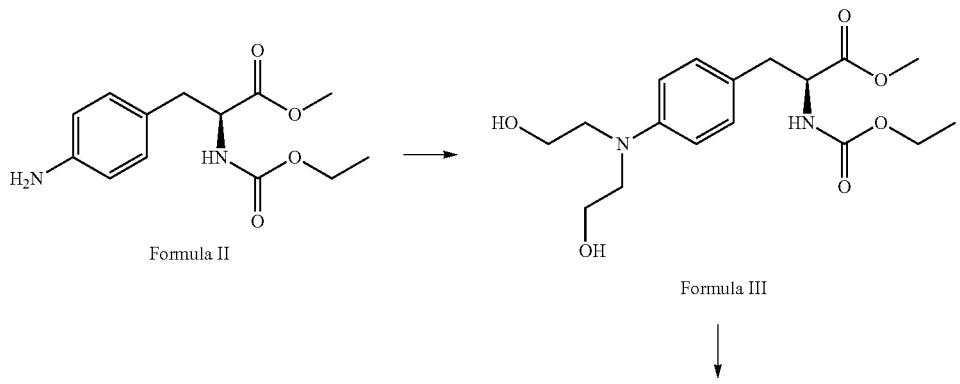

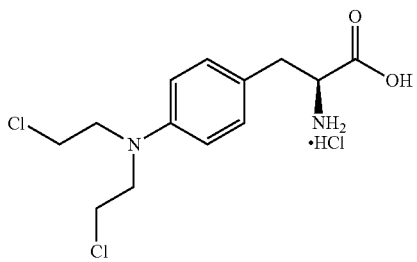

Formula I

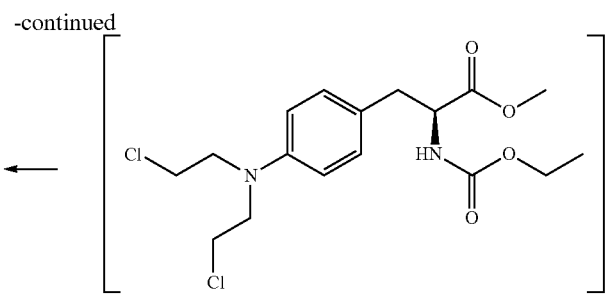

Formula IV

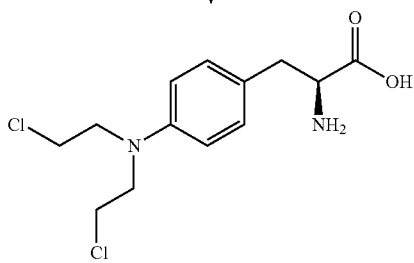

Formula V

Example I (S)-methyl-3-(4-(bis(2-hydroxyethyl)amino)phenyl)-2-(ethoxycarbonylamino)propanoate (Formula III)

50 g of (S)-methyl 3-(4-aminophenyl)-2-(ethoxycarbonylamino)propanoate formula (II) was dissolved in 950 ml water at 40-50° C., and the mixture was cooled to 25-30° C. 80 g of Ethylene oxide gas was passed into the reaction mass and stirred for 15 h at 25-30° C. The precipitated solid was filtered and washed with water. The obtained solid was recrystallized from water and dried to give the title compound as solid (35 g). HPLC: >98%

Example II (S)-2-amino-3-(4-(bis(2-chloroethyl)amino)phenyl) propanoic acid hydrochloride (formula I)

50 g of compound III was slowly added to 115 ml of $POCl_3$ and heated the reaction mixture for 1 h at 85-90° C. After completion of the reaction, $POCl_3$ was distilled out and stripped off the crude with acetonitrile. The reaction mass was cooled to 0-5° C. and 500 ml of concentrated hydrochloric acid was added. Heated the reaction mixture to 100-110° C. and stirred for 10-12 h at the same temperature. Cooled the reaction mass to room temperature and washed with dichloromethane. The aqueous layer was treated with charcoal and filtered through hyflo bed. The pH of the reaction mass was adjusted to 0.3 to 1.2 with sodium acetate solution at about 5° C. and extracted with 1000 ml of ethyl acetate. The solvent was removed under vacuum and to the solid was added acetone (500 ml) and allowed to stir for 6-12 h and the solid filtered and dried under vacuum at 25-30° C. HPLC: >99.5%, any single impurity NMT 0.15%

Example III (S)-2-amino-3-(4-(bis(2-chloroethyl)amino)phenyl) propanoic acid 50 g of (S)-2-amino-3-(4-(bis(2-chloroethyl)amino)phenyl)propanoic acid HCl was suspended in 750 ml of water and cooled to 0-5° C. Adjusted the pH of the reaction to 3.0-5.0 with sodium bicarbonate solution and stirred for 1 hr at 0-5° C. The solid was filtered and washed with water, followed by acetone and the crude product was dried at room temperature for 1 h. The product was then slurried in acetone (500 ml) and filtered and dried at 25-30° C. to give 30 g of the pure product. HPLC: >99.3%

Example IV (S)-2-amino-3-(4-(bis(2-chloroethyl)amino)phenyl) propanoic acid hydrochloride (formula I)

50 g of low purity Melphalan freebase of hydrochloride was dissolved in 500 ml of aqueous hydrochloric acid. The aqueous layer was treated with charcoal and filtered through hyflo bed. The pH of the reaction mass was adjusted to 0.3 to 1.2 with sodium bicarbonate solution at about 5° C. and extracted with 1000 ml of ethyl acetate. The solvent was removed under vacuum and to the solid was added acetone (500 ml) and allowed to stir for 6-12 h and the solid filtered and dried under vacuum at 25-30° C. HPLC: >99.5%, any single impurity NMT 0.15%

We claim:
1. A process for preparation of Melphalan Hydrochloride of formula I

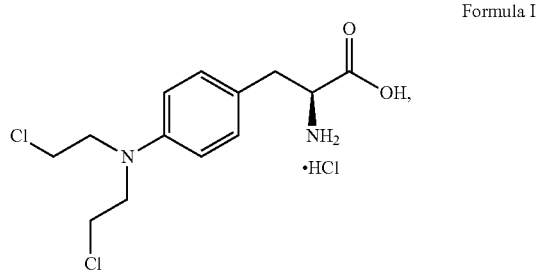 [SMILES: N[C@@H](Cc1ccc(N(CCCl)CCCl)cc1)C(=O)O ; Cl]

Formula I wherein the process is consisting of:
a). chlorinating a compound of formula III

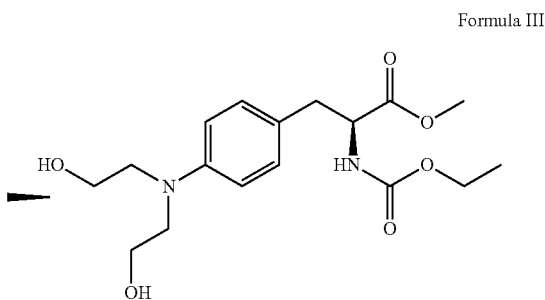

Formula III with thionyl chloride or POCl₃ at about 85-90° C. to obtain a compound of formula IV;

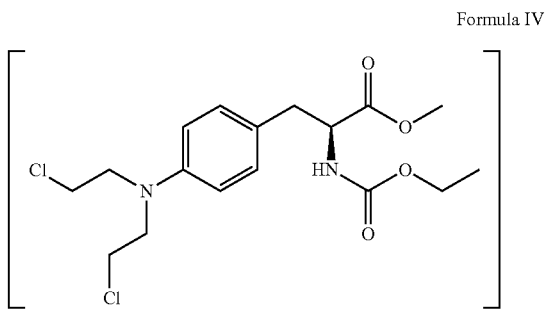

Formula IV b). treating the compound of formula IV with Conc. HCl to hydrolyze the amino and acid protecting groups;
c). cooling the reaction mass to room temperature and washing with dichloromethane;
d). adjusting the pH of the aqueous medium to 0.3 to 1.2;
e). extracting into an organic solvent the Melphalan Hydrochloride of formula I formed, wherein the process is devoid of the formation of Melphalan free base;

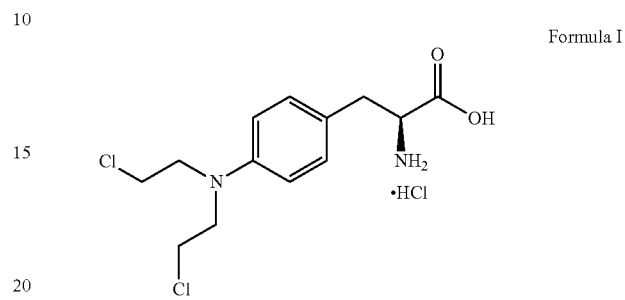

Formula I f). distilling the organic solvent at a temperature range of 25-65° C. to isolate Melphalan hydrochloride of formula I;
wherein the Melphalan hydrochloride of formula I is of greater than 99.5% purity and which has Monohydroxy Melphalan below 0.15%, dihydroxy Melphalan below 0.1% and Melphalan dimer below 0.15%.

2. The process as claimed in claim 1, wherein the organic solvent for extraction is selected from the group comprising ethyl acetate, isopropyl acetate, isobutyl acetate, acetonitrile, dioxane or mixtures thereof.

3. A process for the purification of Melphalan Hydrochloride of formula I, having purity less than 99.5%, wherein the process is consisting of:
a). dissolving Melphalan hydrochloride of formula I or its free base in aqueous hydrochloric acid;
b). adjusting pH of the aqueous medium to 0.3 to 1.2;
c). extracting into an organic solvent the Melphalan Hydrochloride of formula I formed, wherein the process is devoid of formation of Melphalan free base;
d). distilling the organic solvent at a temperature range of 25-65° C. to isolate Melphalan hydrochloride of formula I with greater than 99.5% purity and which has monohydroxy Melphalan below 0.15%, dihydroxy Melphalan below 0.1% and Melphalan dimer below 0.15%.

4. The process as claimed in claim 3, wherein the organic solvent employed in extraction step c) is ethylacetate.

* * * * *